United States Patent [19]

Pilwat et al.

[11] Patent Number: 4,887,434
[45] Date of Patent: Dec. 19, 1989

[54] APPARATUS FOR THE CRYOGENIC ENRICHMENT OF TRACE SUBSTANCES OF A GAS STREAM

[75] Inventors: Gunter Pilwat, Niederzier; Jochen Rudolph, Hürtgenwald, both of Fed. Rep. of Germany

[73] Assignee: Kernforschungsanlage Jülich GmbH, Julich, Fed. Rep. of Germany

[21] Appl. No.: 235,367

[22] Filed: Aug. 23, 1988

[30] Foreign Application Priority Data

Sep. 3, 1987 [DE] Fed. Rep. of Germany ....... 3729374

[51] Int. Cl.⁴ .............................................. B01D 8/00
[52] U.S. Cl. ......................................... 62/55.5; 55/269
[58] Field of Search ............................. 62/55.5; 55/269

[56] References Cited

U.S. PATENT DOCUMENTS

| 3,712,074 | 1/1973 | Boissin | 62/55.5 |
| 3,788,096 | 1/1974 | Brilloit | 62/55.5 |
| 4,506,513 | 3/1985 | Max | 62/55.5 |
| 4,530,250 | 7/1985 | Gay et al. | 73/863.12 |
| 4,666,480 | 5/1987 | Mann | 62/11 |
| 4,668,261 | 5/1987 | Chatzipetros et al. | 62/37 |
| 4,755,201 | 7/1988 | Eschwey | 62/12 |

Primary Examiner—Ronald C. Capossela
Attorney, Agent, or Firm—Herbert Dubno

[57] ABSTRACT

Samples of trace substances are cryogenically concentrated by passing a gas sample through a U-bend immersed in liquid nitrogen. The U-bend is surrounded by a chamber wall and the chamber is vented so that liquid nitrogen can rise into the chamber when the vent is open but is driven out when the vent is closed and the enrichment pipe is heated to desorb the accumulated trace substances from the adsorbent in the enrichment pipe.

9 Claims, 3 Drawing Sheets 4,887,434

APPARATUS FOR THE CRYOGENIC ENRICHMENT OF TRACE SUBSTANCES OF A GAS STREAM

FIELD OF THE INVENTION

Our present invention relates to a device or apparatus for the cryogenic enrichment of trace substances contained in a gas stream, e.g. for analysis by chromatography or the like. More particularly, the invention deals with a method of and an apparatus for concentrating trace substances at least in part by adsorption in the bend of a U-tube which is contacted with a liquid cryogen, such as liquid nitrogen.

BACKGROUND OF THE INVENTION

It is known to concentrate trace substances entrained in a gas by passing the gas stream through a U-shaped tube or pipe, i.e. a U-bend, generally containing an adsorbent, and to immerse the U-bend in a coolant-containing vessel from which the ends of the pipe emerge to connect the U-bend in a pipeline carrying the gas. This method and apparatus have been found to be advantageous for the analysis of traces of hydrocarbons and chlorinated hydrocarbons in gases such as air samples which are drawn for environmental and atmospheric monitoring or for processes control purposes. The analysis usually is carried out by gas chromatography.

Since the limits of detectors for certain trace substances are high, it frequently is necessary to work with sample volumes of a liter or more.

Such large sample volumes, however, cannot be directly fed to a gas chromatograph and thus it has been necessary in the past to carry out a variety of steps to reduce the sample volume and concentrate the trace substances before a sample is injected into the gas chromatograph.

One of the methods used heretofore involves the adsorption and condensation of the trace substances on solid surfaces such as graphite, carbon, silica gel, porous glass beads, organic polymers and like molecular sieve, mechanical or chemical adsorbents, at corresponding low temperatures.

In general, therefore, use could be made of an adsorbent filled tube which had its U-bend immersed in liquid nitrogen in a Dewar flask. A predetermined amount of air was drawn through this enrichment tube and the trace substances which collected on the adsorbent could then be driven off to form the sample for gas chromatographic measurements.

It is also known to bring an enrichment tube in a heat-insulated vessel to a temperature of $-180°$ to $-190°$ C., by spraying it with liquid nitrogen. The enrichment tube may also be made part of a heat exchanger system which is cooled by passing liquid nitrogen through the heat exchanger.

These approaches have, however, a variety of drawbacks. For example, in systems using Dewar flasks, it was generally necessary to manually or mechanically raise and lower the Dewar flask so as to immerse the enrichment tube therein. Cooling by direct spraying with liquid nitrogen is wasteful of the liquid nitrogen since only the latent heat of evaporation of the liquid nitrogen is utilized.

OBJECTS OF THE INVENTION

It is therefore the principal object of the present invention to provide an improved apparatus for the cryogenic concentration of a trace substance in a gas stream which avoids the drawbacks enumerated above.

Another object of this invention is to provide an improved method of concentrating a trace substance from a gas stream utilizing cryogenic principles.

Still another object of the invention is to provide a device or apparatus for the concentration of the trace substances of a gas stream utilizing cryogenic principles, which can operate with a minimum of mechanical effort and involvement, has minimum consumption of liquid nitrogen, can be used for automatic sample enrichment over long periods of time, and can provide a low-cost sample enrichment technique.

SUMMARY OF THE INVENTION

These objects and others which will become apparent hereinafter are attained, in accordance with the present invention utilizing a simplified device which can be integrated into a sample-concentrating apparatus and which can be especially desirable for field measurements, for measurements on ships and for measurements at automated stations.

According to the invention, within the cryogen containing vessel, at least the part of the tube or pipe containing the adsorbent or adapted to collect the trace substance is surrounded by a partition or wall defining a chamber which is open into the vessel at or near the bottom of the latter, while a vent tube extends downwardly into this chamber and is downwardly open while having its upper end, outside the vessel, provided with means for selectively blocking and unblocking this tube. The mouth of the vent tube lies above the aforementioned opening at which the chamber communicates with the remainder of the vessels surrounding it and the device of the invention also comprises means for heating the adsorbent-containing tube or pipe while it remains in the coolant vessel.

By closing of the vent tube, therefore, the liquid cryogen in the chamber can be driven downwardly upon such heating to lower the level of the cryogen immediately surrounding the adsorbent-containing pipe so that the heating of the latter can proceed to drive off the adsorbed trace substance.

More specifically, therefore, the apparatus of the invention can comprise:

a cooling vessel having an upwardly open mouth and adapted to receive a liquid cryogenic coolant;

at least one pipe having at least one U-shaped bend extending into the vessel and having pipe sections connected with the bend extending out of the mouth and connectable in a flow path for the gas stream whereby the trace substance is cryogenically retained in the bend at least in part by adsorption as the gas stream traverses the pipe;

means in the vessel defining a chamber surrounding the U-bend and opening at a location at a lower part of the chamber into the vessel;

a vent tube opening downwardly into the chamber above the location, extending out of the vessel above the mouth and provided externally of the vessel with valve means for opening and closing the vent tube whereby a level of the cryogenic coolant in the chamber can be controlled; and means for heating the trace substance retained in the U-bend to drive the trace substance in concentrated form from the pipe.

In its method aspects, the invention comprises the steps of:

substantially filling a cooling vessel having an upwardly open mouth with a liquid cryogenic coolant;

introducing into the vessel at least one pipe having at least one U-shaped bend extending into the vessel and having pipe sections connected with the bend extending out of the mouth and connectable in a flow path for the gas stream whereby the trace substance is cryogenically retained in the bend at least in part by adsorption as the gas stream traverses the pipe;

defining in the vessel a chamber surrounding the U-bend and opening at a location at a lower part of the chamber into the vessel;

unblocking a vent tube opening downwardly into the chamber above the location, extending out of the vessel above the mouth and provided externally of the vessel with valve means for opening and closing the vent tube to permit a level of the cryogenic coolant to rise in the chamber;

passing the gas stream through the pipe to collect the trace substance in the U-bend; and thereafter heating the trace substance retained in the U-bend to drive the trace substance in concentrated form from the pipe.

Advantageously, the means for heating the pipe may be an electric current source connected across the pipe which, in that case, can be composed of an electrically conductive material so that the pipe acts as a resistance heater. Alternatively, the heating means can include a resistance heater wire wound around the enrichment pipe or a second pipe surrounding the enrichment pipe and composed of an electrically conductive material forming a resistance heater. In the latter case, the enrichment pipe should be composed of quartz. Of course, the heating means can use any combination of these techniques.

The apparatus of the invention makes it possible to alternatively cool and heat the enrichment pipe without the need to discharge all of the liquid nitrogen from the vessel or to remove the enrichment pipe from the coolant vessel.

For cooling of the enrichment pipe to concentrate trace substances from the gas therein, the vent tube is opened to that the lower portion of the chamber fills to the mouth or lower end of the vent tube with liquid nitrogen. Upon termination of the enrichment phase, the vent gas tube is closed and the enrichment pipe is heated. Nitrogen vaporizes in the chamber to drive the liquid nitrogen out of the bottom so that the enrichment pipe is surrounded only by gas and can be quickly heated to the desired final temperature. The trace substances are thereby driven out of the adsorbent.

When heat is again cut off and the vent tube unblocked, liquid nitrogen can return through the chamber opening into the chamber to again bathe the lower part of the U-bend.

The "U-bend" can, of course, form part of a spiral configuration of the enrichment pipe.

It has been found to be advantageous to provide the adsorbent-containing part of the enrichment pipe, i.e. the U-bend or spiral, with a temperature sensor capable of measuring temperatures in the range of 20° to 200° C. to allow the temperature of the pipe to be monitored during the heat phase.

If the enrichment pipe is only filled in the lower portion of its U-bend with adsorbent, the chamber can be so dimensioned that it only surrounds this lower portion of the pipe. The pipe parts which then extend out of the chamber but are still within the coolant vessel will then be jacketed with thermally insulating material.

In the case in which two or more samples are to be enriched simultaneously, the device of the invention can provide a common chamber system from at least two chambers, each receiving a respective enrichment pipe, a vent tube extending into this chamber and respective temperature measuring elements.

The device of the invention is advantageously integrated in an apparatus which comprises a means for establishing a predetermined volume of a gas to be processed connected to one end of the enrichment pipe, the other end of the enrichment pipe being connected in the pipeline. Means can be provided for connecting one of the two ends to a fitting for supplying a carrier gas and the other end to a device for analyzing for the trace substance. The various connecting lines are closable or switchable by appropriate valves.

The device for determining the volume of the gas can include a vacuum pump which is connectable to a vacuum receptacle which can be provided with a vacuum gauge.

BRIEF DESCRIPTION OF THE DRAWING

The above and other objects, features and advantages of my invention will become more readily apparent from the following description, reference being made to the accompanying highly diagrammatic drawing in which:

FIG. 2b is a cross sectional view along the line IIB—IIB of FIG. 2a; and

SPECIFIC DESCRIPTION

Figure 1:
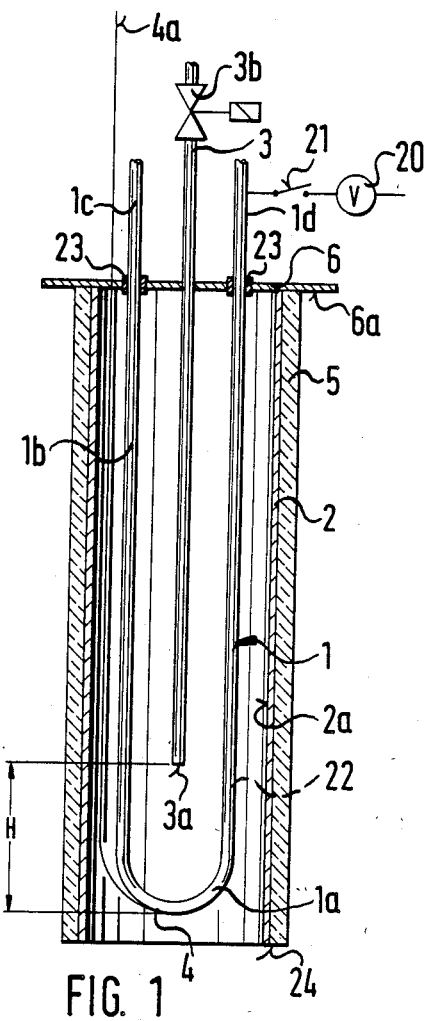
FIG. 1 is a cross sectional view of the device of the invention which can be mounted in a Dewar vessel as shown in FIG. 3, but illustrated without this vessel.
Figure 3:
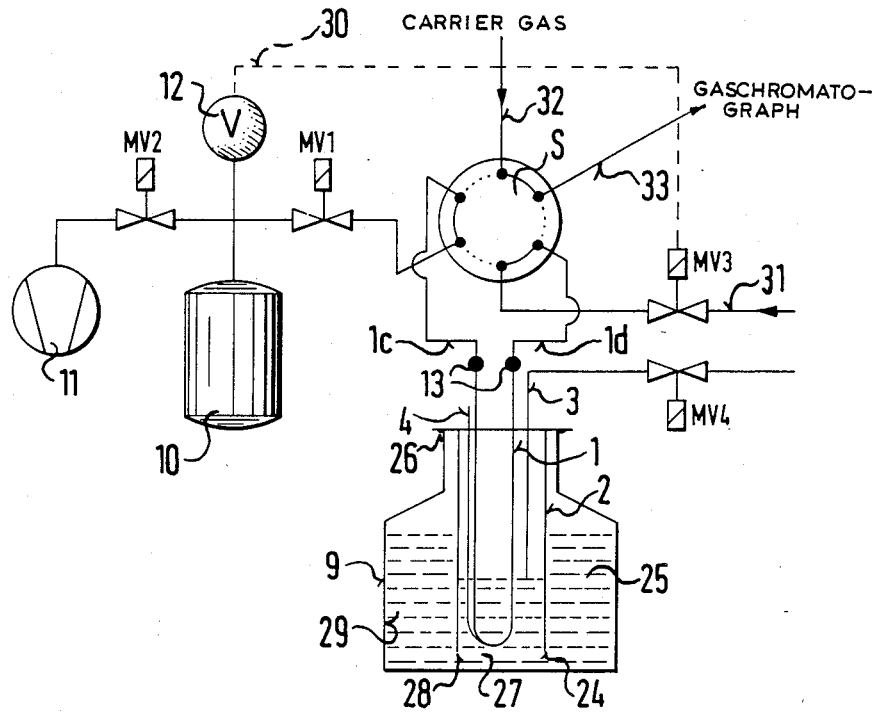
FIG. 3 is a flow diagram illustrating the apparatus of the invention.

FIG. 1 shows in highly diagrammatic form a U-shaped enrichment pipe 1 which can be composed of stainless steel or polytetrafluoroethylene and has a U-bend 1a, two shanks 1b and two ends 1c and 1d adapted to be connected at 13 in an apparatus as shown in FIG. 3, i.e. to a means for passing a gas containing traces of a substance to be concentrated cryogenically through this pipe. In the present embodiment, the pipe is composed of stainless steel and is connectable to a voltage source 20 by a switch 21 so that the pipe because a resistance heater to drive out adsorbed substances. The inner wall of the pipe can be formed, at the bight of the bend, as an adsorbent or, as represented by dots in FIG. 1, the bend to be filled with one of the adsorbents 22 previously described.

The enrichment pipe 1 is associated with a chamber 2 which relatively closely surrounds the pipe and is defined by a cylindrical wall 2a of a stainless steel which is sealed to a flange 6 and is extremely lined by a layer 5 of thermal insulation. The enrichment pipe 1 may be electrically insulated by bushings 23 from the chamber and the ends 1c and 1d can pass out of the flange 6 which sealingly closes the chamber at its upper end.

A conductor 4a runs to a thermal element 4 at the bottom of the bend, this thermal element, sensor or measuring heating may be a Ni-Cr/Ni thermocouple. The conductor 4a, of course, represents a pair of leads of the thermocouple. All elements passing through the flange 6 of the chamber are sealed gas tight and liquid tight relative thereto.

The flange 6 also has a collar 6a adapted to rest upon the mouth of a coolant vessel as has been illustrated diagrammatically in FIG. 3.

A vent tube 3 also extends into the chamber and has a mouth 3a opening above the bottom edge 24 which defines a space with the bottom of the Dewar flask as will be described. The height of the liquid coolant which covers the pipe is thus represented at H in FIG. 1.

Figure 2A:
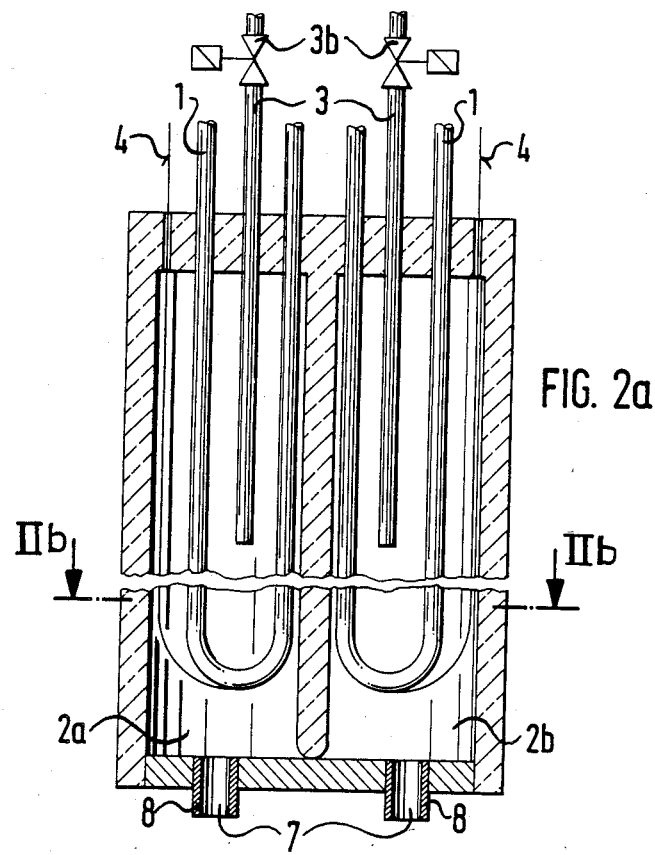
FIG. 2a is a vertical section through a two chamber device in accordance with the invention.
Figure 2B:
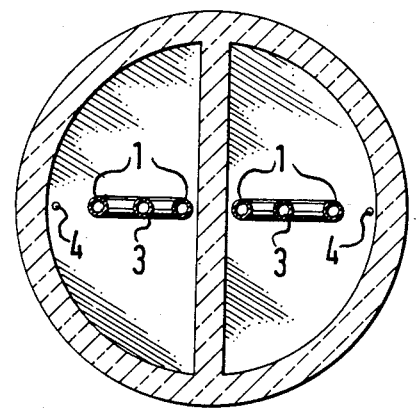

FIGS. 2a and 2b show a two chamber device in which two chambers 2a and 2b are provided.

Each of these chambers is formed independently of the other with an enrichment pipe 1, a vent pipe 3 and its respective valve 3b which can be electromagnetically controlled, a temperature sensor referred to generally at 4, and an opening 7 at the lower part to admit cryogenic coolant into the chamber from the coolant vessel above the bottom of which the device of FIGS. 2 and 2a is suspended.

The chamber system of FIGS. 2a and 2b permits separate enrichment of two samples with each chamber being separately heated or cooled.

Projecting tube segments 8 permit nitrogen gas, which may be driven out of one chamber, from entering the neighboring chamber.

Each chamber can be separately heated or cooled, for example, to allow concentration of trace substances of one sample while another portion is being subjected to chromatographic separation or to allow part of an effluent to be subjected to immediate concentration before being subjected to further chromatographic separation.

The apparatus of FIG. 3 basically comprises a Dewar flask 9 serving as the cooling vessel and shown only diagrammatically. The coolant can be seen at 25 and the Dewar vessel has a lip or rim 26 at its mouth, upon which the collar can rest. The lower edge 24 of the chamber wall lies above the bottom 27 of the coolant container 9 so that an opening 28 is provided between the interior of the chamber 2 and the space 29 of the coolant vessel filled with the liquid nitrogen and surrounding the chamber. In the case of the device of FIGS. 2a and 2b, the device is likewise suspended in a cooling vessel with the bottoms of the tube sections being spaced above the floor of the vessel 9.

One pipe end of the pipe 1 is connected by a 6-way distributing valve S and a magnetic valve MV1 to the vacuum receptacle 10 which may hold a volume of 10 liters.

The vacuum receptacle 10 can be connected by another magnetic valve MV2 with a vacuum pump 11. A vacuum gauge 12 is provided for the vacuum receptacle 10 and has an analog output as represented at 30. The other pipe end is connected via a magnetic valve MV3 with the gas-feed line 31, in this case an airline. The vent pipe 3 here is shown to be provided with the electromagnetic valve MV4. The positions of the valve S has been shown for the enrichment phase. This is also clear from the nitrogen level in the chamber 2. Prior to this phase, valve MV4 has been opened to permit liquid nitrogen to rise in the chamber 2 to the bottom of the vent pipe 3. In this position, air is drawn from inlet 31 via valve MV3 through the pipe 1 so that the trace substance will absorb on the adsorbent of the U-bend, the gas being discharged via valve MV1 to the vacuum vessel 10 which has previously been evacuated by the suction pump 11, valve MV2 then being closed. The valve MV4 can remain open to the atmosphere. The carrier gas meanwhile is delivered by the line 32 and passes to the gas chromatograph via the line 33. Electrical terminals 13 are not connected to the source 20 as yet.

When a full sample has been drawn, the valve S is rotated so that carrier gas is fed to the line 1c while the chromatograph is connected to pipe end 1d, the valve MV4 is closed and the electric current is applied.

The heating of the U-bend causes nitrogen to evaporate in the chamber 2 and drives the liquid outwardly into the coolant vessel through a passage 28. The adsorbent is heated to drive out the concentrated trace substances to the gas chromatograph.

For automatic control of the apparatus, a controller is provided for the 6-way valve S, the magnetic valve MV1, MV2, MV3, MV4, the electric current heat source and the suction pump 11, to respond to the vacuum gauge 12 and the temperature sensor 4.

The control is programmed to effect the following sequence of operations:

Before the beginning of the enrichment phase, all magnetic valves MV1 through MV4 are closed. The 6-way valve is so set that the enrichment pipe 1 is connected to the vacuum receptacle 10 and to the gas feedline 31. The magnetic valve MV2 is first open and the vacuum vessel, whose volume must be known, is evacuated to a final vacuum in the millibar range. Upon attainment of this final vacuum, magnetic valve MV4 is opened. The liquid nitrogen can now rise in the cooling chamber 2 to cool the U-bend of pipe 1 to the liquid nitrogen temperature.

Magnetic valve MV2 to the vacuum pump is then closed and valves MV1 and MV3 are opened. A comparator connected to the analog output 30 of the vacuum gauge 12 controls the valve MV3 until the desired quantity of sampled air has been induced to pass through the pipe 1 and then closes the sample inlet valve.

This magnetic valve can close automatically as the pressure rises to a threshold of about 0.5 bar to prevent the condensation of air in the sample pipe since the partial pressure of air at the temperature of liquid nitrogen is about half of atmospheric pressure. During this interval, of course, trace substances of other gases than air will deposit in the U-pipe the threshold described can be varied to suit the partial pressures of other gases in the sample for which deposition or condensation is not desired.

During this period, moreover, the carrier gas may be passing through the chromatograph.

The injection of the enriched sample in the carrier gas into the gas chromatic range is effected by closing the magnetic valve MC1 and MV4. Valve MV1 separates the sample enrichment pipe 1 from the vacuum container 10 while valve MV4 prevents venting of the chamber 2.

For the desorption of the trace gases, the enrichment pipe 1 is connected as a regulated but direct resistance heater to an electrical current source supplying, for example, 400 amperes at 10 volts. The heating of the pipe 1 vaporizes some of the liquid nitrogen in the chamber 2 to drive the rest of the liquid nitrogen out of this chamber downwardly. The amount of vaporized nitrogen is very small since one ml of liquid nitrogen yields about 700 ml of gas. In the gas-filled space, the pipe is heated to a final temperature of about say 160° C.

under the control of the thermocouple connected to the lower end of the enrichment pipe.

The adsorbent is thus desorbed from the enrichment sample which is carried into the chromatograph upon rotation of the valves through 60°. After the analysis is complete, the 6-way valve and all of the remaining valves are returned to their starting states. The level of liquid nitrogen in the container 9 can be controlled by a level detector and a 10 liter Dewar flask can suffice for the purposes of the invention.

The method and apparatus have no need for mechanical movements such as raising and lowering of the coolant vessel.

We claim:

1. An apparatus for the cryogenic concentration of a trace substance in a gas stream, said apparatus comprising:
   a cooling vessel having an upwardly open mouth and adapted to receive a liquid cryogenic coolant;
   at least one pipe having at least one U-shaped bend extending into said vessel and having pipe sections connected with said bend extending out of said mouth and connectable in a flow path for said gas stream whereby said trace substance is retained in said bend at least in part by adsorption as said gas stream traverses said pipe;
   means in said vessel defining a chamber surrounding said U-bend and opening at location at a lower part of said chamber into said vessel;
   a vent tube opening downwardly into said chamber above said location, extending out of said vessel above said mouth and provided externally of said vessel with valve means for opening and closing said vent tube whereby a level of said liquid cryogenic coolant in said chamber can be controlled; and
   means for heating the trace substance retained in said U-bend to drive the trace substance in concentrated form from said pipe.

2. The apparatus defined in claim 1 wherein said means for heating said trace substance retained in said U-bend includes means for connecting said pipe to an electric current source, said pipe being electrically conductive to form a resistance heater when electric current is passed therethrough.

3. The apparatus defined in claim 1, further comprising an electric temperature sensor responsive to temperature in a region at which said trace substance is adsorbed in said U-bend, and a conductor connected to said sensor and extending out of said chamber and said vessel.

4. The apparatus defined in claim 3 wherein said chamber forms one of two chambers formed in a common body and each receiving a respective said U-bend, vent tube and sensor, and receivable in said vessel.

5. The apparatus defined in claim 1, further comprising:
   means for determining a volume of the gas stream to be passed through said pipe connected to one end of said pipe;
   valve means for feeding a carrier gas to an end of said pipe; and
   valve means for connecting an end of said pipe to an analyzer responsive to said trace substance.

6. The apparatus defined in claim 5 wherein said means for determining a volume comprises an evacuatable receptacle and a vacuum source connected to said receptacle.

7. The apparatus defined in claim 6, further comprising a vacuum gauge connected to said evacuatable receptacle.

8. The apparatus defined in claim 1, further comprising an adsorbent for said trace substance received in said U-bend.

9. A process for the cryogenic concentration of a trace substance in a gas stream, comprising the steps of:
   substantially filling a cooling vessel having an upwardly open mouth with a liquid cryogenic coolant;
   introducing into said vessel at least one pipe having at least one U-shaped bend extending into said vessel and having pipe sections connected with said bend extending out of said mouth and connectable in a flow path for said gas stream whereby said trace substance is cryogenically retained in said bend at least in part by adsorption as said gas stream traverses said pipe;
   defining in said vessel a chamber surrounding said U-bend and opening at location at a lower part of said chamber into said vessel;
   unblocking a vent tube opening downwardly into said chamber above said location, extending out of said vessel above said mouth and provided externally of said vessel with valve means for opening and closing said vent tube to permit a level of said cryogenic coolant to rise in said chamber;
   passing said gas stream through said pipe to collect said trace substance in said U-bend; and
   thereafter heating the trace substance retained in said U-bend to drive the trace substance in concentrated form from said pipe.

* * * * *